(12) United States Patent
Stalcup et al.

(10) Patent No.: US 9,707,080 B2
(45) Date of Patent: Jul. 18, 2017

(54) REMOVABLE AUGMENT FOR MEDICAL IMPLANT

(71) Applicant: SMed-TA/TD, LLC, Columbia City, IN (US)

(72) Inventors: Gregory C. Stalcup, Columbia City, IN (US); Troy D. Knapp, Alachua, FL (US)

(73) Assignee: SMed-TA/TD, LLC, Columbia City, IN (US)

(*) Notice: Subject to any disclaimer, the term of this patent is extended or adjusted under 35 U.S.C. 154(b) by 0 days.

(21) Appl. No.: 15/231,000

(22) Filed: Aug. 8, 2016

(65) Prior Publication Data

US 2016/0338837 A1 Nov. 24, 2016

Related U.S. Application Data

(62) Division of application No. 14/204,862, filed on Mar. 11, 2014, now Pat. No. 9,408,699.

(Continued)

(51) Int. Cl.
*A61F 2/38* (2006.01)
*A61F 2/28* (2006.01)
(Continued)

(52) U.S. Cl.
CPC ........ *A61F 2/2846* (2013.01); *A61F 2/30734* (2013.01); *A61F 2/38* (2013.01); *A61F 2/389* (2013.01); *A61F 2/3859* (2013.01); *A61F 2002/3092* (2013.01); *A61F 2002/30433* (2013.01); *A61F 2002/30736* (2013.01);
(Continued)

(58) Field of Classification Search
CPC ...... A61F 2/389; A61F 2/3868; A61F 2/3859; A61F 2/38; A61F 2/2846
See application file for complete search history.

(56) References Cited

U.S. PATENT DOCUMENTS 3,855,638 A 12/1974 Pilliar
3,867,728 A 2/1975 Stubstad et al.
(Continued)

FOREIGN PATENT DOCUMENTS

WO 03/026714 A1 4/2003
WO 2008/040408 A1 4/2008

OTHER PUBLICATIONS

Bryan, R.S. et al. "The Effect of Polyvinyl-Formal (Ivalon) Sponge on Cortical Bone Healing." Proceedings of the Staff Meetings of The Mayo Clinic vol. 33 (1958): 453-457 (3 pages).
(Continued)

*Primary Examiner* — Jason-Dennis Stewart
(74) *Attorney, Agent, or Firm* — Taylor IP, P.C.

(57) ABSTRACT

A method of using an orthopedic implant includes providing a main body, as well as a porous augment having a bone ingrowth surface. The main body is removably attached with another surface of the porous augment to form an orthopedic implant. A portion of a bone is extracted from the body of a patient and, subsequently, the orthopedic implant is implanted into the body of the patient. The porous augment is positioned such that a bone interfacing surface of the porous augment interfaces with a cut surface of the bone from which the portion of bone is extracted to facilitate bone ingrowth into the porous augment.

7 Claims, 3 Drawing Sheets

Related U.S. Application Data

(60) Provisional application No. 61/787,598, filed on Mar. 15, 2013.

(51) Int. Cl.
*A61F 2/30* (2006.01)
*A61F 2/46* (2006.01)

(52) U.S. Cl.
CPC .......... *A61F 2002/4619* (2013.01); *A61F 2310/00359* (2013.01)

(56) References Cited

U.S. PATENT DOCUMENTS

| | | | |
|---|---|---|---|
| 4,011,602 A | 3/1977 | Rybicki et al. | |
| 4,222,128 A | 9/1980 | Tomonaga et al. | |
| 4,608,052 A | 8/1986 | Van Kampen et al. | |
| 4,737,411 A | 4/1988 | Graves, Jr. et al. | |
| 4,769,041 A | 9/1988 | Morscher | |
| 4,846,834 A | 7/1989 | von Recum et al. | |
| 4,976,738 A | 12/1990 | Frey et al. | |
| 5,030,233 A | 7/1991 | Ducheyne | |
| 5,104,410 A | 4/1992 | Chowdhary | |
| 5,204,055 A | 4/1993 | Sachs et al. | |
| 5,219,363 A | 6/1993 | Crowninshield et al. | |
| 5,282,861 A | 2/1994 | Kaplan | |
| 5,370,693 A | 12/1994 | Kelman | |
| 5,380,328 A | 1/1995 | Morgan | |
| 5,490,962 A | 2/1996 | Cima et al. | |
| 5,496,372 A | 3/1996 | Hamamoto et al. | |
| 5,518,680 A | 5/1996 | Cima et al. | |
| 5,531,793 A | 7/1996 | Kelman | |
| 5,549,685 A | 8/1996 | Hayes | |
| 5,571,187 A | 11/1996 | Devanathan | |
| 5,637,175 A | 6/1997 | Feygin et al. | |
| 5,730,817 A | 3/1998 | Feygin et al. | |
| 5,732,469 A | 3/1998 | Hamamoto et al. | |
| 5,755,800 A | 5/1998 | O'Neil et al. | |
| 5,807,406 A | 9/1998 | Brauker et al. | |
| 5,869,170 A | 2/1999 | Cima et al. | |
| 5,876,550 A | 3/1999 | Feygin et al. | |
| 6,010,336 A | 1/2000 | Shimotoso et al. | |
| 6,136,029 A | 10/2000 | Johnson et al. | |
| 6,139,574 A | 10/2000 | Vacanti et al. | |
| 6,143,035 A | 11/2000 | McDowell | |
| 6,176,874 B1 | 1/2001 | Vacanti et al. | |
| 6,306,424 B1 | 10/2001 | Vyakarnam et al. | |
| 6,328,765 B1 | 12/2001 | Hardwick et al. | |
| 6,333,029 B1 | 12/2001 | Vyakarnam et al. | |
| 6,337,198 B1 | 1/2002 | Levene et al. | |
| 6,365,149 B2 | 4/2002 | Vyakarnam et al. | |
| 6,409,764 B1 | 6/2002 | White et al. | |
| 6,423,252 B1 | 7/2002 | Chun et al. | |
| 6,440,734 B1 | 8/2002 | Pykett et al. | |
| 6,461,385 B1 | 10/2002 | Gayer et al. | |
| 6,471,993 B1 | 10/2002 | Shastri et al. | |
| 6,514,514 B1 | 2/2003 | Atkinson et al. | |
| 6,526,984 B1 | 3/2003 | Nilsson et al. | |
| 6,527,810 B2 | 3/2003 | Johnson et al. | |
| 6,530,958 B1 | 3/2003 | Cima et al. | |
| 6,533,818 B1 | 3/2003 | Weber et al. | |
| 6,534,084 B1 | 3/2003 | Vyakarnam et al. | |
| 6,544,472 B1 | 4/2003 | Compton et al. | |
| 6,554,857 B1 | 4/2003 | Zilla et al. | |
| 6,571,130 B1 | 5/2003 | Ljungstrom et al. | |
| 6,599,322 B1 | 7/2003 | Amrich et al. | |
| 6,626,950 B2 | 9/2003 | Brown et al. | |
| 6,673,108 B2 | 1/2004 | Zilla et al. | |
| 6,712,850 B2 | 3/2004 | Vyakarnam et al. | |
| 6,783,546 B2 | 8/2004 | Zucherman et al. | |
| 6,852,272 B2 | 2/2005 | Artz et al. | |
| 6,881,413 B1 | 4/2005 | Bartholeyns | |
| 6,893,465 B2 | 5/2005 | Huang | |
| 6,993,406 B1 | 1/2006 | Cesarano, III et al. | |
| 7,018,418 B2 | 3/2006 | Amrich et al. | |
| 7,052,710 B2 | 5/2006 | Giordano et al. | |
| 7,087,200 B2 | 8/2006 | Taboas et al. | |
| 7,108,828 B2 | 9/2006 | Lefebvre et al. | |
| 7,174,282 B2 | 2/2007 | Hollister et al. | |
| 7,189,409 B2 | 3/2007 | Pirhonen et al. | |
| 7,208,222 B2 | 4/2007 | Rolfe et al. | |
| 7,250,060 B2 | 7/2007 | Trieu | |
| 7,531,190 B2 | 5/2009 | Kumar et al. | |
| 7,537,617 B2 | 5/2009 | Bindsell et al. | |
| 7,537,664 B2 | 5/2009 | O'Neill et al. | |
| 7,632,228 B2 | 12/2009 | Brauker et al. | |
| 7,666,230 B2 | 2/2010 | Orban et al. | |
| 7,674,426 B2 | 3/2010 | Grohowski, Jr. | |
| 7,674,477 B1 | 3/2010 | Schmid et al. | |
| 2002/0072798 A1 | 6/2002 | Riesle et al. | |
| 2003/0171820 A1 | 9/2003 | Wilshaw et al. | |
| 2004/0191292 A1 | 9/2004 | Chou | |
| 2005/0038435 A1 | 2/2005 | Cole et al. | |
| 2005/0100578 A1 | 5/2005 | Schmid et al. | |
| 2005/0177247 A1 | 8/2005 | Canham et al. | |
| 2005/0228503 A1 | 10/2005 | Gundolf | |
| 2005/0246032 A1 | 11/2005 | Bokros et al. | |
| 2006/0178744 A1 | 8/2006 | de Villiers et al. | |
| 2006/0241776 A1 | 10/2006 | Brown et al. | |
| 2006/0282166 A1 | 12/2006 | Molz et al. | |
| 2007/0038299 A1 | 2/2007 | Stone et al. | |
| 2007/0105222 A1 | 5/2007 | Wolfinbarger et al. | |
| 2007/0129809 A1 | 6/2007 | Meridew et al. | |
| 2007/0185585 A1 | 8/2007 | Bracy et al. | |
| 2007/0190880 A1 | 8/2007 | Dubrow et al. | |
| 2007/0191963 A1 | 8/2007 | Winterbottom et al. | |
| 2007/0196419 A1 | 8/2007 | Teller et al. | |
| 2007/0203584 A1 | 8/2007 | Bandyopadhyay et al. | |
| 2009/0024161 A1 | 1/2009 | Bonutti | |
| 2009/0204225 A1 | 8/2009 | Meridew et al. | |
| 2010/0042167 A1 | 2/2010 | Nebosky et al. | |
| 2010/0042215 A1 | 2/2010 | Stalcup et al. | |
| 2010/0042218 A1 | 2/2010 | Nebosky et al. | |
| 2010/0190254 A1 | 7/2010 | Chian et al. | |
| 2010/0222889 A1* | 9/2010 | Howling .................. A61F 2/38 623/20.21 |
| 2010/0291286 A1 | 11/2010 | O'Neill et al. | |
| 2011/0035018 A1 | 2/2011 | Deffenbaugh et al. | |
| 2011/0064784 A1 | 3/2011 | Mullens et al. | |
| 2011/0106268 A1 | 5/2011 | Deffenbaugh | |
| 2011/0153028 A1 | 6/2011 | Albertorio | |
| 2011/0190899 A1 | 8/2011 | Pierce et al. | |
| 2011/0202141 A1 | 8/2011 | Metzger et al. | |
| 2012/0101591 A1 | 4/2012 | Servidio | |
| 2012/0310361 A1* | 12/2012 | Zubok .................. A61F 2/30734 623/20.32 |
| 2013/0013077 A1 | 1/2013 | Metzger | |

OTHER PUBLICATIONS

Galante, J. et al. "Sintered Fiber Metal Composites as a Basis for Attachment of Implants to Bone" Journal of Bone and Joint Surgery Am 53 (1971):101-114 (15 pages).

Bobyn, J.D., Pilliar, R.M., Cameron, H.U., and Weatherly, G.C. "The Optimum Pore Size for Fixation of Porous-Surfaced Metal Implants by the Ingrowth of Bone." Clinical Orthopedics and Related Research. 150 (1980): 263-270 (8 pages).

Bobyn, J.D., Stackpool, G.J., Hacking, S.A., Tanzer, M., and Krygier, J.J. "Characteristics of Bone Ingrowth and Interface Mechanics of a New Porous Tantalum Biomaterial." The Journal of Bone & Joint Surgery (Br) vol. 81-B (1999): 907-914 (8 pages).

Hulbert, S.F., Young, F.A., Mathews, R.S., Klawitter, J.J., Talbert, C.D., Stelling, F.H. "Potential of Ceramic Materials as Permanently Implantable Skeletal Prostheses." Journal of Biomedical Materials Research. 4 (1970): 433-456 (24 pages).

Levine, B. "A New Era in Porous Metals: Applications in Orthopaedics." Advanced Engineering Materials. 10 (2008): 788-792 (5 pages).

"Biofoam Technical Monograph", Cancellous Titanium Matrix, Fixation with Bite, Wright Medical, 2009.

Notification of Transmittal of the International Search Report and the Written Opinion of the International Searching Authority, or the

(56) References Cited

OTHER PUBLICATIONS

Declaration dated Jul. 4, 2014 for International Application No. PCT/US2014/026090 (14 pages).
International Preliminary Report on Patentability and the Written Opinion dated Sep. 15, 2015 for International Application No. PCT/EP2014/026090 (9 pages).
Extended European Search Report dated Oct. 26, 2016 for European Patent Application No. 14 77 0377 (7 pages).

* cited by examiner

REMOVABLE AUGMENT FOR MEDICAL IMPLANT

CROSS REFERENCE TO RELATED APPLICATIONS

This is a division of U.S. patent application Ser. No. 14/204,862, entitled "REMOVABLE AUGMENT FOR MEDICAL IMPLANT", filed Mar. 11, 2014, which is incorporated herein by reference. U.S. patent application Ser. No. 14/204,862, is a non-provisional application based upon U.S. Provisional Patent Application Ser. No. 61/787,598, entitled "POROUS ORTHOPAEDIC AUGMENTS", filed Mar. 15, 2013, which is incorporated herein by reference.

BACKGROUND OF THE INVENTION

1. Field of the Invention

The present invention relates to medical implants, and, more particularly, to medical implants with a bone in-growth surface.

2. Description of the Related Art

Orthopaedic implants are medical devices used for replacing or providing for stabilization and fixation of a bone or for replacement of articulating surfaces of a joint. The need for surgery requiring the implantation of such a medical device is usually the result of osteoarthritis, also known as degenerative joint disease, or injury. In the past, such orthopaedic implants have been formed of a solid, biocompatible material, which have been utilized with the goal of giving the patient an improved quality of life with reduced pain and inflammation, as well as increased stability, mobility and directed flexibility. Additionally, orthopaedic implants are known which have a rigidly attached, hard porous surface, which allows for minimal tissue ingrowth. Further, with each successive orthopaedic surgery, more and more of the natural bone is often removed.

What is needed in the art is a medical implant which improves stabilization of the implant through bone ingrowth over time and which reduces the amount of natural bone which must be removed during the course of successive revision surgeries.

SUMMARY OF THE INVENTION

The present invention provides an orthopaedic augment including a porous material which is removably attached to a medical implant. The porous material provides a bone ingrowth surface for interfacing with an existing bone material.

The present invention further provides an orthopaedic implant including a main body and a porous augment which is removably attached to the main body. The porous augment has a bone ingrowth surface for interfacing with a bone material. Another surface of the porous augment is coupled with the main body of the orthopaedic implant.

Additionally, the present invention provides a method of using the orthopaedic implant, which includes providing a main body, as well as a porous augment having a bone ingrowth surface. The main body is removably attached with another surface of the porous augment to form an orthopaedic implant. A portion of a bone is extracted from the body of a patient and, subsequently, the orthopaedic implant is implanted into the body of the patient. The porous augment is positioned such that a bone interfacing surface of the porous augment interfaces with a cut surface of the bone from which the portion of bone is extracted to facilitate bone ingrowth into the porous augment.

An advantage of the present invention is that the present invention provides orthopaedic augments and implants that aid in the process of rebuilding bone by utilizing the porous surface to permit subsequent bone growth into the pores of the augment. The use of porous material, which permits bone ingrowth, provides a more reliable fixation and aids in rebuilding the bone in the event of a subsequent required revision surgery.

An additional advantage of the present invention is that during a subsequent revision surgery, the augment and ingrown bone can be cut through, instead of cutting through additional natural bone mass during the course of each successive surgery, as is the current practice. The present invention also provides for the provision of augments of different shapes and sizes such that the augment can be easily reconfigured or formed to meet a set of specific circumstances.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrates embodiments of the invention and such exemplifications are not to be construed as limiting the scope of the invention in any manner.

DETAILED DESCRIPTION OF THE INVENTION

Figure 1:
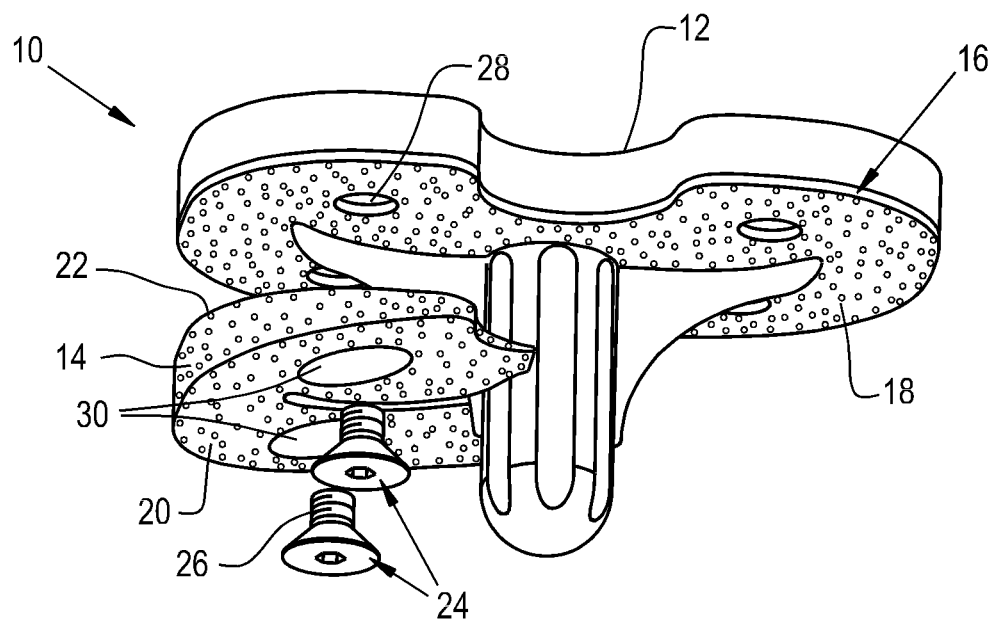
FIG. 1 is an exploded view of a tibial tray with an augment according to the present invention.
Figure 2:
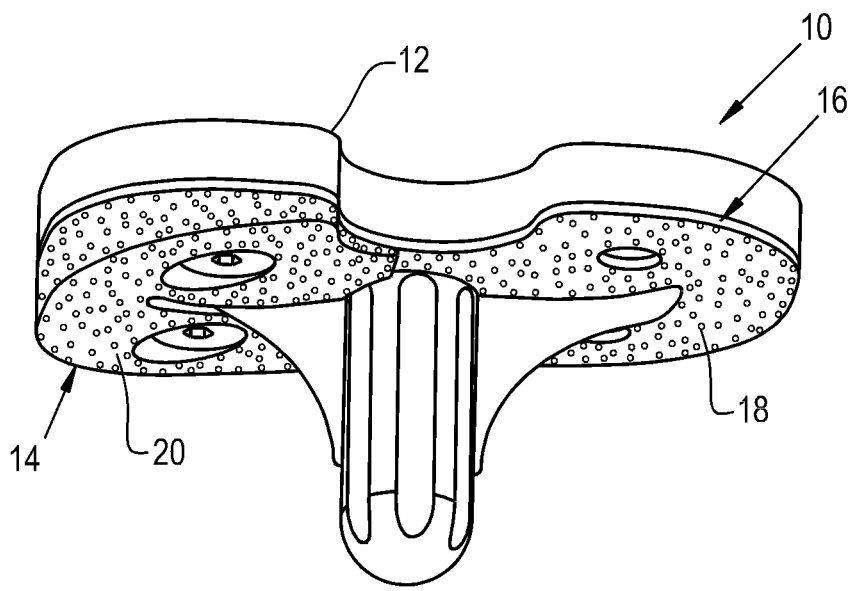
FIG. 2 is an assembled perspective view of the tibial tray with the augment illustrated in FIG. 1.

Referring now to the drawings, and more particularly to FIGS. 1 and 2, there is shown an orthopaedic implant 10, which generally includes a main body 12 and an orthopaedic augment 14.

The main body 12 is illustrated in FIGS. 1 and 2 as a tibial tray, however, it may be any conventional total or partial orthopaedic implant. The main body 12 is formed of a biocompatible material, for example, metals such as alumina, titanium and titanium alloys, tantalum and tantalum alloys, cobalt chrome alloys, stainless steel, as well as biocompatible polymers such as polyaryletherketone (PAEK) and polyetheretherketone (PEEK). Main body 12 may further include a rigidly attached, optional porous layer 16 on the bone facing side 18 of the main body 12. Porous layer 16 may be formed, for example, of beads, mesh, lattice, etc.

Orthopaedic augment 14 is formed of a porous material, and more particularly from any suitable clinically usable, biocompatible porous material. Exemplary materials include porous polymer materials including polyetheretherketone (PEEK), polymer scaffolds, allograft bone, authograft bone, easily cut metal scaffold, or other similar bone or tissue ingrowth surfaces. Orthopaedic augment 14 includes a porous ingrowth surface 20 for interfacing with existing bone material and another surface 22 for interfacing with main body 12. Although only one orthpaedic augment 14 is shown in combination with main body 12, any number of orthopaedic augments 14 may be provided for use with main body 12, for example at least one, two, three, or four or more.

Orthopaedic augment 14 is removably attachable with main body 12 by a mechanical apparatus, adhesion or bonding. For example, as illustrated in FIGS. 1 and 2, orthopaedic augment 14 is removably attached to main body 12 using fasteners 24, for example screws 24 including a plurality of threads 26 adapted to thread into a respective threaded hole or opening 28 in main body 12. In this embodiment, orthopaedic augment 14 includes a bore 30 through which fastener 24 is passed, bore 30 being positioned to correspond with opening 28 in main body 12. Bore 30 may be formed with a countersink to accommodate the fasteners 24, for example in the case of a screw, such that the screw head is positioned flush with or below the surface of the augment 14. Any number of fasteners 24 and corresponding bores 30 and threaded openings 28 may be provided for implant 10. Fasteners 24 are also formed of a biocompatible material, for example, PEEK, or any known biocompatible polymeric material or metallic material.

Figure 3:
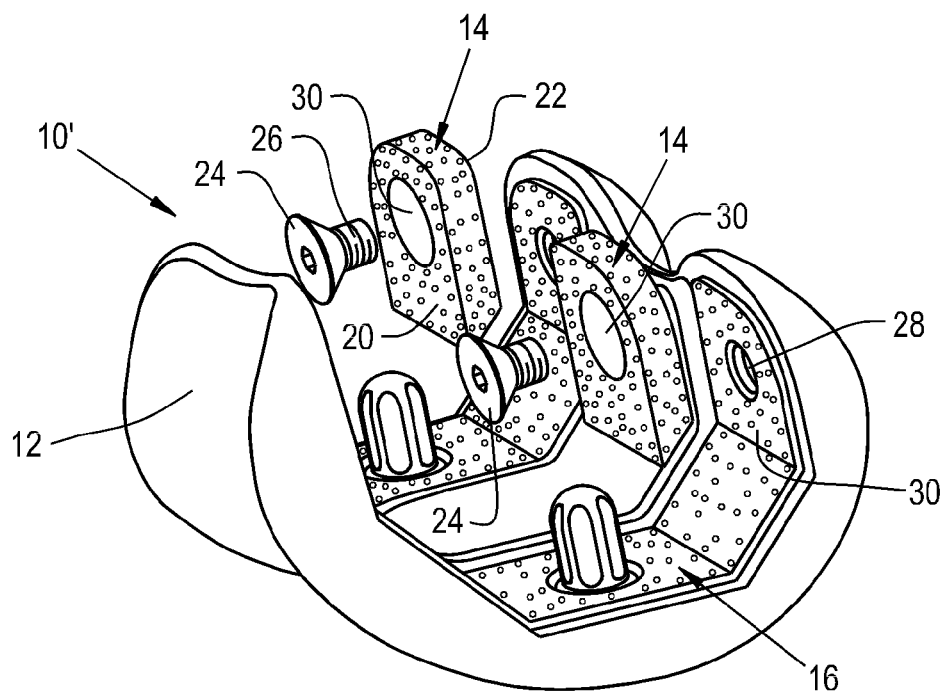
FIG. 3 is an exploded view of femoral implant with a pair of posterior augments according to the present invention.
Figure 4:
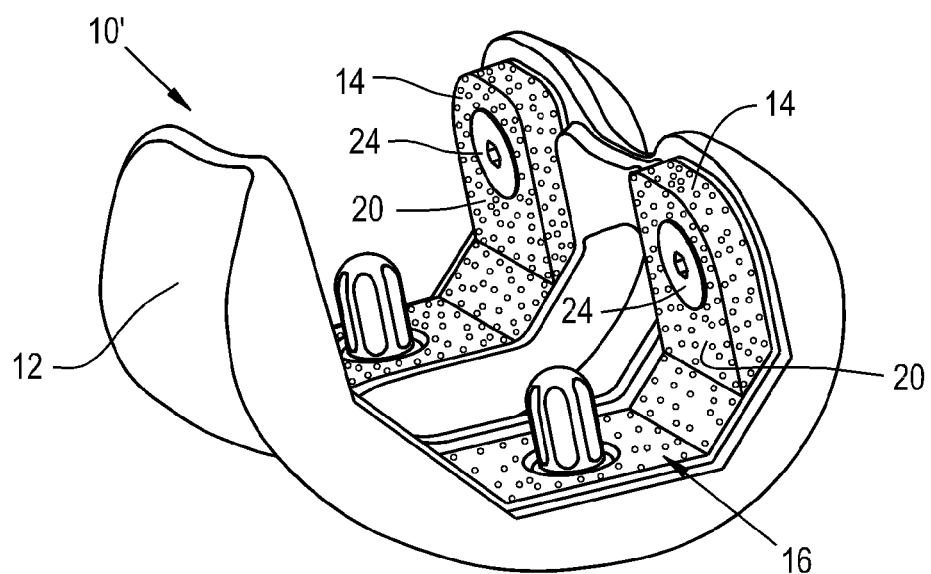
FIG. 4 is an assembled prospective view of the femoral implant with the pair of posterior augments illustrated in FIG. 3.
Figure 5:
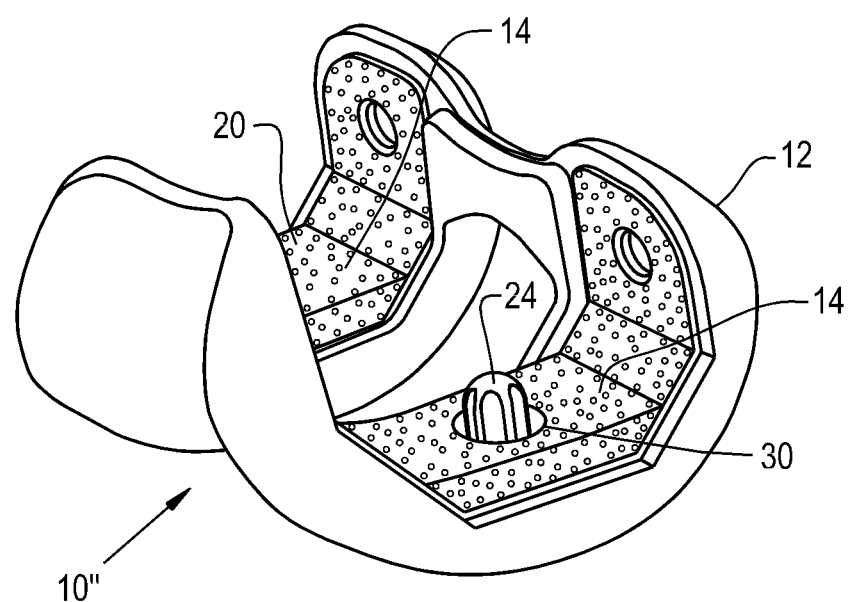
FIG. 5 is a prospective view of a femoral implant with a distal augment according to the present invention.

Referring now to FIGS. 3 and 4, there is shown an additional embodiment of the orthopaedic implant according to the present invention in the form of a femoral implant 10'. Femoral implant 10' includes main body 12 and a pair of orthopaedic augments 14. Main body 12 is shown here as including an optional porous layer 16, as described more fully above with respect to the implant 10, illustrated in FIGS. 1 and 2. In FIGS. 3 and 4, orthopaedic augments 14 are removably attached to main body 12 using a pair of fasteners 24 (screws 24) inserted through corresponding bores 30. Screws 24 again include threads 26 adapted to thread into a respective threaded opening 28 in main body 12. Although the orthopaedic augments 14 of the present invention are shown in FIGS. 3 and 4 as being positioned on a posterior surface 30 of main body 12 with a corresponding screw 24, the positioning of the orthopaedic augments 14 within main body 12, as well as the number of fasteners 24 utilized for securing orthopaedic augments 14 to main body 12, are unrestricted. For example, referring now to FIG. 5, an orthopaedic implant in the form of a femoral implant 10", is shown including main body 12 with porous layer 16, to which a pair of porous orthopaedic augments 14 are each attached with a single fastener 24 in the form of a centrally positioned stake or post 24 on a distal surface of main body 12.

The present orthopaedic augment and orthopaedic implants according to the present invention allow for bone ingrowth, such that should subsequent revision surgery be required, the combination of added bone material and porous augment may be cut through, as opposed to sacrificing more bone during the course of each successive surgery. The orthopaedic augment and orthopaedic implants of the present invention may be utilized for purposes of any primary or revision orthpaedic surgery.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of using an orthopaedic implant, the method comprising the steps of:
providing a main orthopaedic implant body;
providing a porous augment having a bone ingrowth surface;
removably attaching said main orthopaedic implant body with another surface of said porous augment to form an orthopaedic implant;
extracting a portion of a bone from a body of a patient;
subsequent to said extracting step, implanting said orthopaedic implant into the body of the patient;
positioning said porous augment such that a bone interfacing surface of said porous augment interfaces with a cut surface of said bone from which said portion is extracted and to facilitate bone ingrowth;
forming an opening in the cut surface of said bone; and
placing a post of said orthopaedic implant in said formed opening, said post having a solid exposed surface.

2. The method of using an orthopaedic implant according to claim 1, wherein said step of removably attaching said other surface of said porous augment with said main orthopaedic implant body is with at least one fastener.

3. The method of using an orthopaedic implant according to claim 2, wherein said at least one fastener is formed from polyether ether ketone (PEEK).

4. The method of using an orthopaedic implant according to claim 1, said porous augment being one of a polymer scaffold, allograft bone, autograft bone, and a cuttable metal scaffold.

5. The method of using an orthopaedic implant according to claim 1, said porous augment being formed from polyether ether ketone (PEEK).

6. The method of using an orthopaedic implant according to claim 1, further comprising the step of cutting a predetermined segment of said orthopaedic augment and an ingrown bone material during a revision surgery.

7. The method of using an orthopaedic implant according to claim 1, further comprising the step of detaching said main orthopaedic implant body from said porous augment.

* * * * *